(12) United States Patent
Turtz

(10) Patent No.: US 11,420,031 B2
(45) Date of Patent: Aug. 23, 2022

(54) SYSTEM AND METHOD FOR DRAINING CEREBROSPINAL FLUID IN HYDROCEPHALUS PATIENTS

(71) Applicant: Alan Richard Turtz, Cherry Hill, NJ (US)

(72) Inventor: Alan Richard Turtz, Cherry Hill, NJ (US)

( * ) Notice: Subject to any disclaimer, the term of this patent is extended or adjusted under 35 U.S.C. 154(b) by 545 days.

(21) Appl. No.: 16/154,062

(22) Filed: Oct. 8, 2018

(65) Prior Publication Data

US 2019/0105476 A1    Apr. 11, 2019

Related U.S. Application Data

(60) Provisional application No. 62/569,832, filed on Oct. 9, 2017.

(51) Int. Cl.

| *A61M 25/00* | (2006.01) |
| *A61M 27/00* | (2006.01) |
| *A61B 5/03* | (2006.01) |
| *A61B 5/00* | (2006.01) |
| *A61B 5/083* | (2006.01) |

(Continued)

(52) U.S. Cl.
CPC ......... *A61M 27/006* (2013.01); *A61B 5/0031* (2013.01); *A61B 5/031* (2013.01); *A61M 25/0068* (2013.01); *A61B 5/021* (2013.01); *A61B 5/024* (2013.01); *A61B 5/0836* (2013.01); *A61B 5/4561* (2013.01);

(Continued)

(58) Field of Classification Search
CPC ....... A61B 5/0031; A61B 5/021; A61B 5/024; A61B 5/031; A61B 5/0836; A61B 5/4561; A61M 2025/0073; A61M 2202/0464; A61M 2210/0693; A61M 25/0068; A61M 27/006
See application file for complete search history.

(56) References Cited

U.S. PATENT DOCUMENTS

| 4,363,395 A | 12/1982 | Redmond et al. |
| 5,980,480 A * | 11/1999 | Rubenstein ......... A61M 27/006 604/9 |

(Continued)

OTHER PUBLICATIONS

International Search Report for related PCT/US2018/054821 dated Dec. 17, 2018.

*Primary Examiner* — Kai H Weng
(74) *Attorney, Agent, or Firm* — The Belles Group, P.C.

(57) ABSTRACT

A system and related method are provided for draining cerebrospinal fluid from a bodily cavity of a patient, such as a ventricle in the brain in one application. The system includes a reservoir which may be a collapsible container configured for fluidic connection to a shunt located in the bodily cavity. The collapsible container may be an elastically deformable bladder in one embodiment. A pump is fluidly connected to the collapsible container and draws cerebrospinal fluid therefrom. A programmable controller directs the pump to repeatedly activate and deactivate at a predetermined time interval. A plurality of sensors may be provided which are communicably coupled to the controller for monitoring pump motor current draw, tension in the resilient body of the container, pressure, and orientation of the patient. The controller is configurable to deactivate the pump when abnormal operating conditions are detected by the sensors.

17 Claims, 7 Drawing Sheets

(51) Int. Cl.
    *A61B 5/021*          (2006.01)
    *A61B 5/024*          (2006.01)

(52) U.S. Cl.
    CPC ............ *A61M 2025/0073* (2013.01); *A61M 2202/0464* (2013.01); *A61M 2210/0693* (2013.01)

(56) References Cited

U.S. PATENT DOCUMENTS

| | | |
|---|---|---|
| 6,638,208 B1 | 10/2003 | Natarajan et al. |
| 2003/0099548 A1 | 5/2003 | Meza et al. |
| 2006/0212097 A1 | 9/2006 | Varadan et al. |
| 2009/0318844 A1 | 12/2009 | Burnett |
| 2010/0076366 A1* | 3/2010 | Henderson, Sr. ...... A61B 5/076 |
| | | 604/9 |
| 2013/0197422 A1* | 8/2013 | Browd ................ A61M 27/006 |
| | | 604/9 |
| 2015/0094644 A1* | 4/2015 | Lenihan ................ A61M 39/24 |
| | | 604/9 |

* cited by examiner

SYSTEM AND METHOD FOR DRAINING CEREBROSPINAL FLUID IN HYDROCEPHALUS PATIENTS

CROSS-REFERENCE TO RELATED APPLICATIONS

The present application claims the benefit of U.S. Provisional Application No. 62/569,832 filed Oct. 9, 2017; the entirety of which is incorporated herein by reference.

FIELD

The present invention relates to the treatment of hydrocephalus. Particular embodiments of the invention relate to systems and methods for draining cerebrospinal fluid in patients with normal pressure hydrocephalus.

BACKGROUND

Hydrocephalus is the buildup of cerebrospinal fluid (CSF) in the cavities (ventricles) deep within the brain. The excess fluid increases the size of the ventricles and puts pressure on, and/or deforms the brain. Normally, CSF flows through the ventricles and over the brain and spinal column. The accumulation of too much CSF associated with hydrocephalus can damage brain tissues and cause a large range of impairments in brain function. Although hydrocephalus can occur at any age, it's more common among infants and older adults.

Surgical treatment for hydrocephalus can restore and maintain normal CSF levels in the brain. One such treatment involves the placement of a tube from the brain to another part of the body, called a "shunt," which allows the excess CSF to flow away from the brain and thus prevent deformation and/or excessive pressure in the brain.

Hydrocephalus can be categorized as high pressure hydrocephalus (HPH) or normal pressure hydrocephalus (NPH). High pressure hydrocephalus is caused by too much CSF volume causing an increase in intracranial pressure and will usually deform the brain. High pressure hydrocephalus is primarily a pressure problem. Normal pressure hydrocephalus is caused by too much CSF volume that does not cause an increase in intracranial pressure and always deforms the brain. Normal pressure hydrocephalus is a volume problem.

Normal pressure hydrocephalus is a type of hydrocephalus that usually occurs in older adults. NPH is different than other types of hydrocephalus in that it develops slowly over time. The drainage of CSF is blocked gradually, and the excess fluid builds up slowly. The slow enlargement of the ventricles means that the fluid pressure in the brain may not be as high as in other types of hydrocephalus. However, the enlarged ventricles still press on the brain and can cause symptoms, as a result, the term "normal pressure" can be somewhat misleading.

There are different causes of NPH such as subarachnoid hemorrhage, tumor, head trauma and infection. These kinds of NPH can develop sub-acutely. Slow development is common in idiopathic NPH, the condition that typically affects older adults for reasons that are not understood. In addition, NPH itself is poorly understood.

All shunts that use a tube to divert CSF from the brain to another body cavity require a one-way valve mechanism. All valves currently available are passive, which makes them prone to siphon effects, resulting in over drainage. All valves currently available require a pressure threshold or gradient to open and are, therefore, pressure dependent. High pressure hydrocephalus patients have a pressure problem, for which pressure dependent valves are designed. Normal pressure hydrocephalus patients have a volume problem, for which pressure dependent valves are not designed. The inability to drain a precise volume of CSF is a problem and can result in complications secondary to over drainage, or inadequate treatment secondary to under drainage.

Accordingly, improved systems and methods for draining the proper amount of CSF from the brain, particularly in NPH patients, are needed.

SUMMARY

A CSF drainage control system according to the present disclosure actively removes excess CSF from the brain of a patient at a precise rate, including an NPH patient, without subjecting the brain to negative pressure and monitors the drainage process to increase the safety of the patient. Although many of the examples of the invention discussed herein are tailored to treating NPH, embodiments of the invention can also be used in patients with HPH. For NPH, the present system advantageously does not rely on a pressure-activated valve to drain CSF from the ventricles of the patient. Instead, an active pump fluidly communicating with the drainage shunt emplaced in the brain operates to draw CSF therefrom.

The use an active pump to drain CSF can result in negative pressure on the brain tissue if the ventricles are collapsed, unless some type of safety shut off is provided. A collapsed ventricle can collapse around the catheter and cut off fluid flow to the shunt. Embodiments of the invention provide an expandable and collapsible reservoir (effectively a "fifth ventricle") that acts as a safety shutoff to prevent the brain tissue from being subjected to negative pressure. The reservoir is fluidly interconnected between the shunt and pump. The reservoir, or alternatively collapsible container, may be a resiliently deformable and stretchable bladder in one embodiment formed of a material having an elastic memory. When in a fully or terminally collapsed state, the bladder is configured and structured to tightly seal off the fluid passageway from the shunt to the bladder, thereby advantageously fluidly isolating the internal volume of the bladder and pump from the shunt to prevent subjecting the brain tissue to negative pressure.

It bears noting that the negative pressure that the drainage system will avoid is on the brain tissue if the ventricles collapse. The system may generate minute, transient and clinically insignificant negative changes in pressure when it pumps fluid out of the ventricles. A benefit of the present CSF drainage system invention is that if the ventricles collapse for any reason and limit the amount of fluid available to the bladder, negative pressure will not be transmitted to the brain tissue surrounding the ventricles.

In one aspect, a system for draining cerebrospinal fluid from a bodily cavity of a patient includes: a collapsible container configured to be fluidly connected to a shunt that is located in the brain for draining cerebrospinal fluid; a pump fluidly connected to the collapsible container; and a programmable controller that directs the pump to repeatedly activate and deactivate to draw cerebrospinal fluid from the collapsible container. In one embodiment, the programmable controller may control and direct the pump to activate and deactivate at a preprogrammed predetermined time interval and run for a predetermined period of time at a flowrate which draws a set volume from the container. In one embodiment, the bodily cavity may be a ventricle in the brain of the patient. In other embodiments, the bodily cavity may be from the lumbar thecal sac into the peritoneal cavity and the shunt may thus be a lumbar-peritoneal shunt. Drainage of CSF from other portions of the body may be performed using the present drainage system.

In another aspect, a system for draining cerebrospinal fluid from a brain of a patient includes: a deformable reservoir changeable between an expanded condition and collapsed condition; a cerebrospinal fluid drainage passageway formed between the brain and the reservoir to collect cerebrospinal fluid in the reservoir; and a pump fluidly connected to the reservoir and operable to draw cerebrospinal fluid therefrom; wherein the deformable reservoir is configured and operable to fluidly isolate the fluid passageway from the pump when the deformable reservoir is in the collapsed condition.

In another aspect, a method for draining cerebrospinal fluid from a bodily cavity of a patient includes: draining the cerebrospinal fluid from a shunt in the brain to a deformable collapsible container, the collapsible container changeable between a collapsed state and an expanded state; pumping the cerebrospinal fluid from the collapsible container with a pump fluidly connected to the collapsible container; and repeatedly activating and deactivating the pump at a predetermined time interval with a programmable controller.

Further areas of applicability of the present invention will become apparent from the detailed description provided hereinafter. It should be understood that the detailed description and specific examples, while indicating non-limiting preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Figure 1:
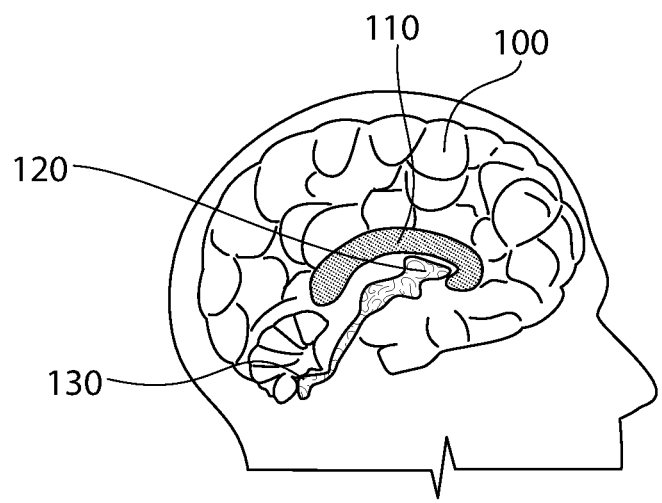
FIG. 1 is partial sectional view of a normal brain.

All drawings are schematic and not necessarily to scale. Parts given a reference numerical designation in one figure may be considered to be the same parts where they appear in other figures without a numerical designation for brevity unless specifically labeled with a different part number and described herein.

DETAILED DESCRIPTION

The following description of the preferred embodiment(s) is merely exemplary in nature and is in no way intended to limit the invention, its application, or uses.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "connected," "coupled," "interconnected," and similar refer to a relationship wherein structures are secured or attached to one another either directly or indirectly through intervening structures, as well as both movable or rigid attachments or relationships, unless expressly described otherwise. The term "fixed" refers to two structures that cannot be separated without damaging one of the structures. The term "filled" refers to a state that includes completely filled or partially filled.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

As explained above, hydrocephalus is the buildup of cerebrospinal fluid (CSF) in the cavities (ventricles) deep within the brain. The excess fluid increases the size of the ventricles and puts pressure on, and/or deforms the brain. Normally, CSF flows through the ventricles and over the brain and spinal column The accumulation of too much CSF associated with hydrocephalus can damage brain tissues and cause a large range of impairments in brain function.

FIG. 1 shows an example of a human brain 100 and normal size ventricles. The brain has four ventricles, two lateral ventricles 110 (only the right side lateral ventricle is shown as superimposed on the left side lateral ventricle), a third ventricle 120, and a fourth ventricle 130. In FIG. 1 the four ventricles are shown a normal size that would result from a normal CSF pressure and volume.

Figure 2:
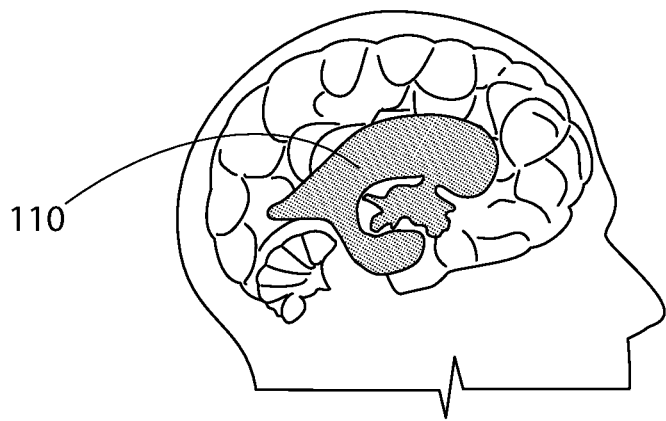
FIG. 2 is a partial sectional view of a brain with hydrocephalus.

FIG. 2 shows brain 100 suffering from hydrocephalus. In FIG. 2, lateral ventricle 110 is shown enlarged due to an excess of CSF. This condition would exert increased pressure and/or deformation of brain 100 that can result in damage to brain 100.

Figure 3:
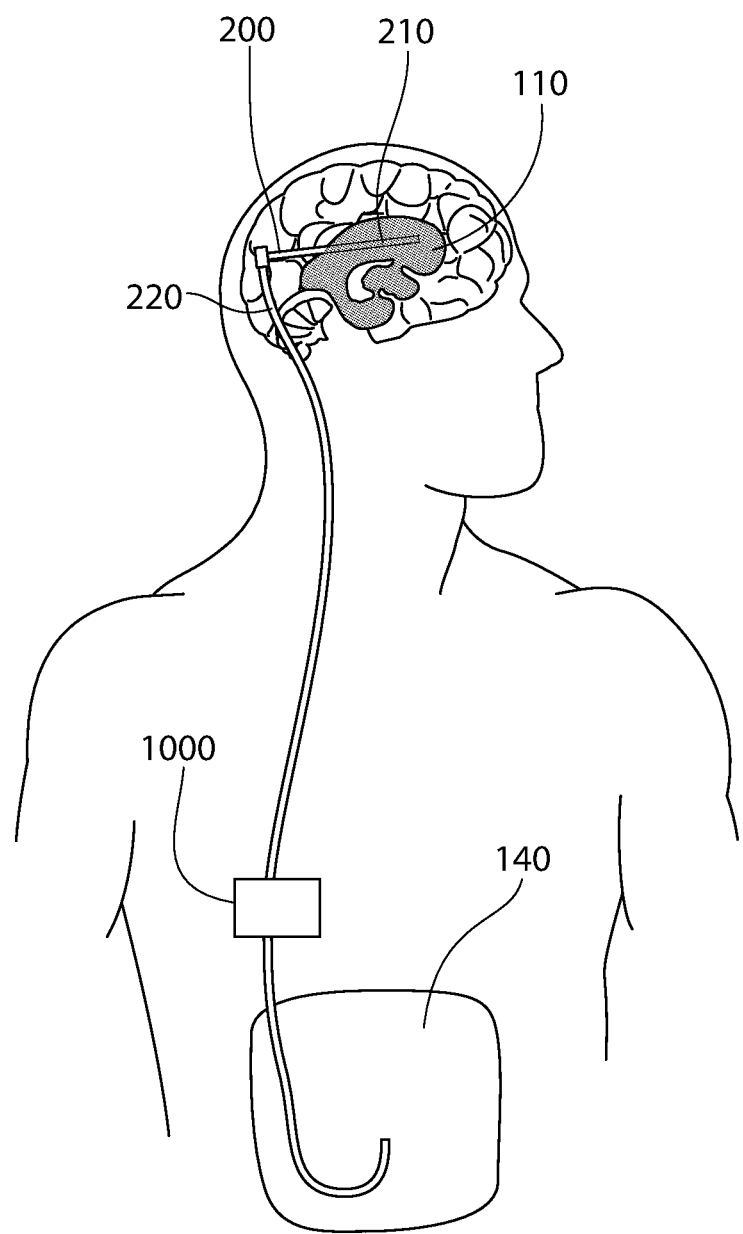
FIG. 3 is a partial sectional view of an installed system in accordance with exemplary embodiments of the invention.

FIG. 3 shows an example of a system that drains excess CSF from the brain in order to prevent excess pressure and/or deformation and the resulting damage. Such a system is surgically implanted in the body and is, in most cases, permanent. The example shown in FIG. 3 includes a draining apparatus 200 that channels the CSF from the brain to drainage control system 1000. Draining apparatus 200 include a ventricular catheter 210 that has one end implanted into a ventricle (for example a lateral ventricle 110) and an opposite end that is attached to a drain line 220. Drain line 220 can be run subcutaneously under the skin of the neck, chest, and abdomen from ventricular catheter 210 to drainage control system 1000. A further drain line 1030/1040 is provided to channel the CSF from drainage control system 1000 to a suitable repository or cavity in the body such as, for example, peritoneum 140.

Drainage control system 1000 includes, in this example, a number of elements that combine to provide periodic drainage of the CSF from the brain. Unlike other systems, drainage control system 1000 (and other systems and methods in accordance with embodiments of the invention) drains the CSF based on time and/or volume and not based on pressure. This provides successful draining in cases of normal pressure hydrocephalus that cannot be handled properly with pressure-based systems.

As explained above, some conventional treatment systems and methods use a passive, intracranial pressure dependent valve to regulate the amount of CSF that drains out of the brain. The passive pressure dependent valve is subject to siphon effect and is poorly suited to patients having normal pressure hydrocephalus (NPH). These NPH patients are at risk of inconsistent and insufficient drainage, as well as over drainage which can cause serious complications.

Systems and methods of the invention provide an electronic, mechanical device that actively drains a specifically programmed volume of CSF at a precise flow rate that prevents active suction from being transmitted to the brain tissue. This replaces the conventional passive, pressure dependent valve.

Particular embodiments of the invention include an electromechanical volume regulated pump that incorporates a safety mechanism which allows passive flow from the brain directly into a resiliently/elastically deformable reservoir. The reservoir can have intrinsic material properties which prevent active suction on the brain, thereby providing the safety mechanism. For example, the reservoir can be an expandable bladder-like reservoir that expands and contracts depending on the volume of CSF in the reservoir. Other constructions of the reservoir can also be used if they prevent active suction on the brain tissue. With the reservoir eliminating the danger of active suction being transmitted to the brain tissue, an implantable active electromechanical pump can be used. The active pump can be programmed to drain CSF at precise volumes and flow rates. This programming, along with interrogation, can take place transcutaneously by a technician, or caregiver. The reservoir limits any siphon effect that could have been generated by the pump by having an expandable and collapsible volume that prevents negative pressure from being transmitted to the brain tissue. The system also permits non-invasive precise measurement of intracranial pressure, and can detect (and alarm) when a shunt malfunction occurs, which can alert the patient and/or caregiver to seek medical attention before clinical symptoms and signs develop.

In addition to patients with normal pressure hydrocephalus, embodiments of the invention have clinical utility in selected patients with other types of hydrocephalus where precise control of CSF volume and flow rates are necessary, when siphon effects need to be eliminated, and/or when precise intracranial pressure (ICP) measurements and built-in warning systems are desired.

Figure 4:
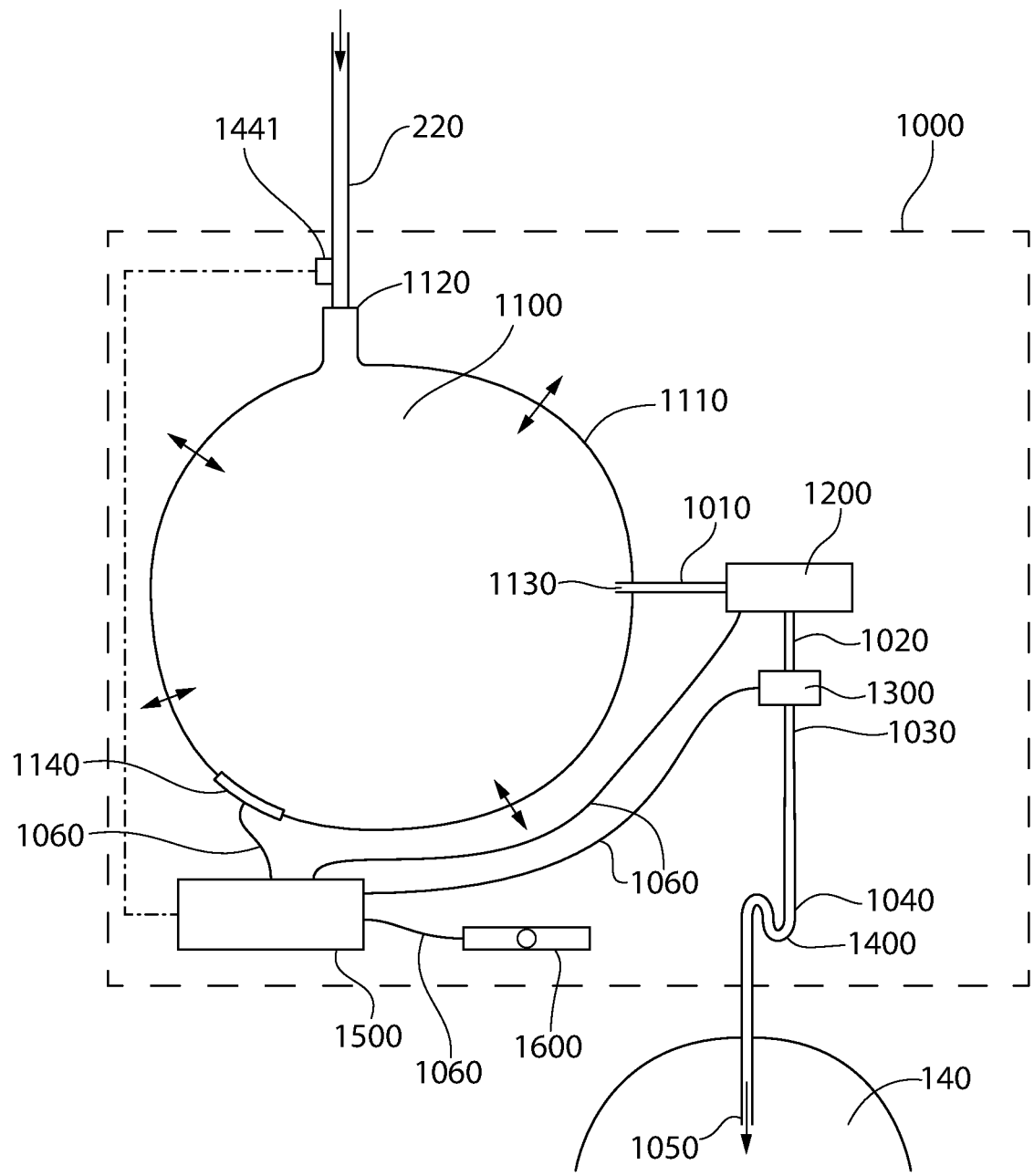
FIG. 4 is a schematic view of a system in accordance with exemplary embodiments of the invention.

FIG. 4 shows a schematic representation of a drainage control system 1000 in accordance with an exemplary embodiment of the invention. System 1000 has an elastically deformable expandable and collapsible reservoir 1100 (alternatively "container") that receives CSF by way of drain line 220 from ventricular catheter 210. Reservoir 1100 effectively acts as a "fifth ventricle" that can be controlled by a healthcare provider. Reservoir 1100 comprises a bladder body 1110 in one non-limiting embodiment that is made of a resilient and elastically flexible material such as, for example, silicone, or other elastic biocompatible material preferably having an elastic memory. Accordingly, preferred embodiments of the bladder body are formed of a pliable non-rigid material. An internal variable volume is defined by the stretchable and collapsible walls that form the bladder body 1110. The bladder body 1110 (alternatively referred to herein as "bladder" for brevity) may be without limitation generally circular in shape (as shown), cylindrical, irregularly shaped, or have yet other shapes. The use of irregular shaped bladders would allow reliable occlusion of the outflow tract, and less likely the inflow tract, with relatively small volume changes within the bladder. The shape of the bladder does not limit the invention.

Bladder body 1110 has an inlet 1120 that is fluidly connected to drain line 220 at, for example, the upper area of bladder body 1110. The drain line 220 is fluidly coupled to shunt 210, which collectively form a drainage passageway from the brain to the bladder. Bladder body 1100 has an outlet 1130 for CSF to be removed from bladder body 1110 by a pump unit 1200. In this example, pump unit 1200 is fluidly connected to bladder body 1110 by a fluid line 1010. While outlet 1130 is shown in an approximately central location on bladder body 1110, other locations of outlet 1130 can also be used. Unlike with a fixed volume container (where an outlet needs to be near the bottom of the container), the expandable/collapsible nature of bladder body 1110 with elastic memory permits the outlet to be placed at almost any location on bladder body 1110. This is due to bladder body 1110 collapsing as fluid is drawn out of bladder body 1110 by pump unit 1200, and thereby pushing the fluid upwards (in this example) as the bladder body 1110 collapses. In some embodiments, the capacity of bladder body 1110 in an inflated, but unbiased, state is equal to or greater than the volume of CSF pumped by the pump in one pumping cycle (discussed in more detail below).

The deformable bladder 1110 has a normal relaxed state or condition when neither expanded by CSF nor collapsed. Bladder 1110 is changeable between an expanded state or condition (e.g. stretched state) and a collapsed state or condition. Each of these is further described herein.

Reservoir 1100 is shown having one or more sensors 1140. Non-exclusory examples of sensors that can be provided include volume sensors, stretch sensors, and pressure sensors. A volume sensor can be provided to determine the amount of fluid present in reservoir 1100. Such sensors can include, for example, float switches, radiofrequency sensors, conductivity sensors, or other sensors. A stretch sensor can be provided and attached to the bladder body 1110 to determine if bladder body is in a relaxed state, a stretched (expanded) state, and/or a collapsed state including a terminally collapsed state. If bladder body 1110 is in a stretched state, then the fluid in bladder body 1110 must be under pressure, which could indicate a problem that needs to be addressed. Such stretch sensors can include, for example, piezoelectric strain gauges, and electroactive polymer capacitive stretch sensors. A pressure sensor can be used to determine if the fluid in reservoir 1100 is under pressure. Such sensors can include, for example, piezoelectric strain gauges, capacitive sensors, electromagnetic sensors, and optical sensors. The output from these sensors can be transmitted to a controller 1500 by a communication link or conduit 1060 which can be, for example, any suitable type of communication link/conduit such as for example without limitation a wire, optical fiber, or a wireless connection (e.g. Bluetooth, Near Field Communication, etc.). The controller can use this information to control operation of the pump unit 1200, one-way valve 1300, or other aspects of the CSF drainage system. The function of controller 1500 is discussed in detail below.

In some embodiments, a backup safeguard to the bladder body 1110 may be provided to prevent exposing the ventricles in the brain to negative pressure produced by the suction of the pump unit 1200 in the event of an abnormal operating condition or failure of the bladder. The backup safeguard may comprise a pressure sensor 1141 attached to and operable to sense pressure in the drain line 220 between the shunt 210 and reservoir 1100. Pressure sensor 1141 is communicably coupled to controller 1500. In the event sensor 1141 detects formation of a negative pressure in drain line 220 which meets or exceed a preprogrammed setpoint negative pressure, the controller is configured to automatically deactivate the pump unit 1200 to prevent transmittance of the negative pressure induced by the pump operation to the brain.

Figure 6:
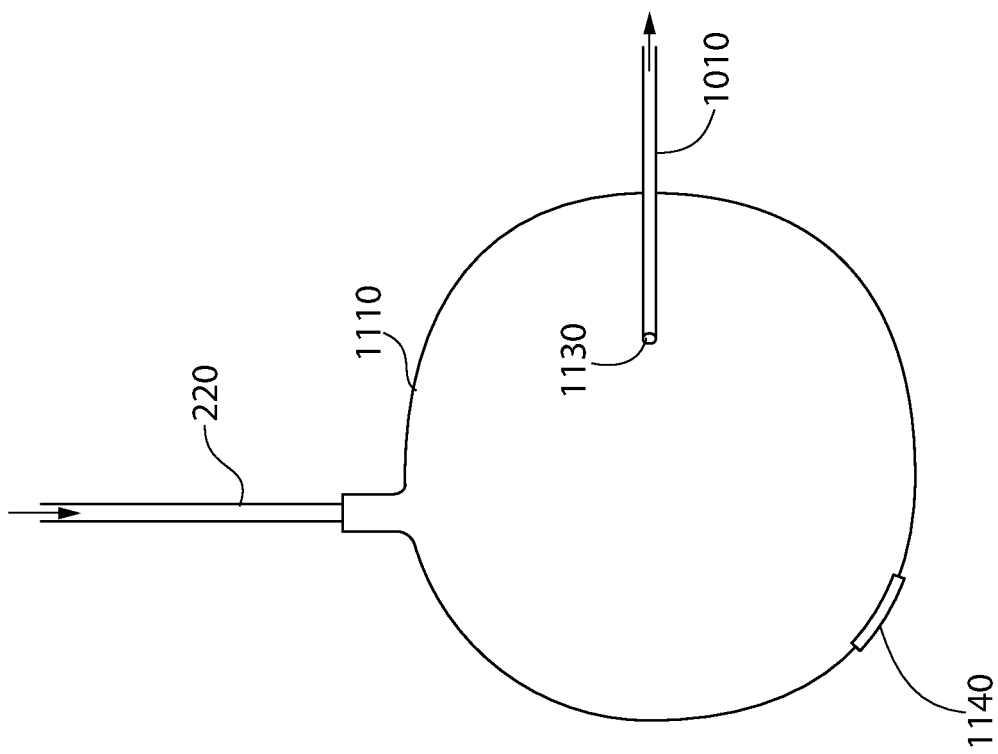
FIG. 6 is a schematic view of a fluid reservoir in accordance with exemplary embodiments of the invention in an expanded state.
Figure 5:
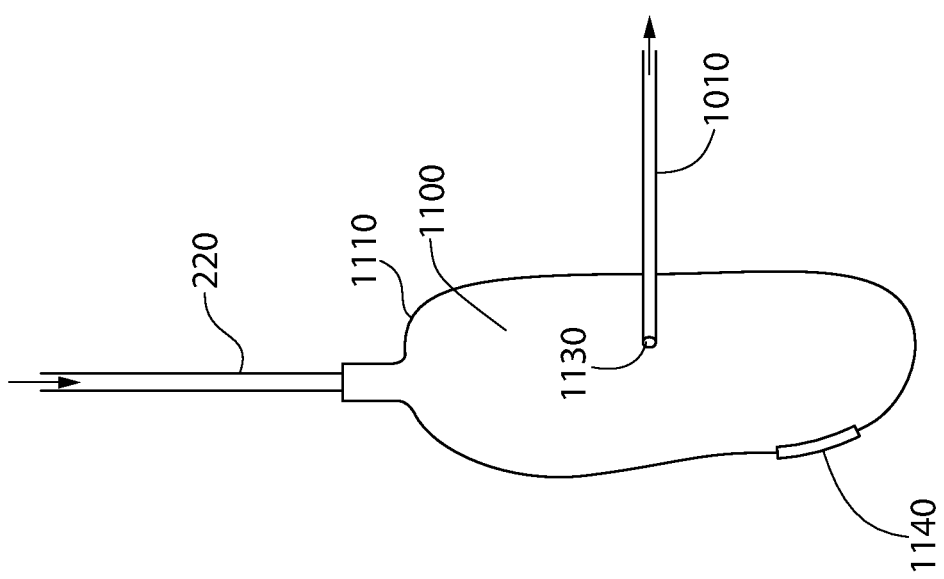
FIG. 5 is a schematic view of a fluid reservoir in accordance with exemplary embodiments of the invention in a relaxed state.

FIG. 5 shows a side view of the elastically deformable reservoir 1100 in a relaxed state (where the pressure inside bladder body 1110 is equal to the pressure outside bladder body 1110). The bladder body 1110 is essentially undeformed. FIG. 6 shows a side view of reservoir 1100 in a stretched or expanded state due to the presence of CSF in the reservoir (where the pressure inside bladder body 1110 is greater than the pressure outside bladder body 1110). In the stretched state shown in FIG. 6, one or more of sensors 1140 would send a signal to controller 1500 to indicate the stretched condition. It is noted that the pressure inside bladder body 1110 in a relaxed state can be slightly different than the ICP (intracranial pressure) due to the difference in vertical location of bladder body 1110 relative to the brain.

Figure 7:
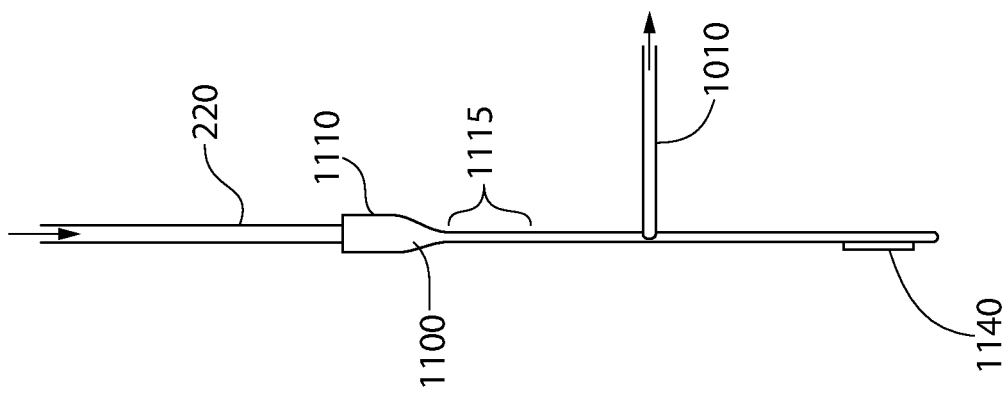
FIG. 7 is a schematic view of a fluid reservoir in accordance with exemplary embodiments of the invention in a collapsed and occluded state.

FIG. 7 shows a side view of reservoir 1100 in a fully/terminally collapsed (or occluded) state. In the collapsed state, the suction from pump unit 1200 cannot reach the brain because reservoir 1100 is collapsed to the point of cutting off the fluid path between pump unit 1200 and the brain. This condition prevents the brain from being subjected to negative pressure. The collapsible bladder body 1110 of the reservoir 1100 thus acts as a pressure control device to fluidly isolate the pump unit from the brain when a negative pressure is formed within the reservoir caused by suction from the pump unit. In this example embodiment, the one-piece monolithic deformable bladder body 1110 itself is self-occluding and comprises an integral occluding portion 1115 that collapses, and therefore completely cuts off the fluid path, more easily than other parts of bladder body 1110. The occluded portion 1115 therefore is structured to more readily deform than remaining portions of bladder body 1110 in order to facilitate complete closure of the fluid path in a sealed manner. Occluding portion 1115 can be a thinned unitary portion of the monolithic wall of bladder body 1110, or an intentionally creased portion of the monolithic wall of bladder body 1110, or some other configuration formed in the monolithic wall that collapses and occludes the flow path more easily than other portions of the unitary monolithic body of the bladder. It bears noting that foregoing structures in a reliantly deformable and one-piece monolithic self-occluding body are distinguishable from a mechanical valve having multiple components which might be considered to have an occluded state when the valve closure member (e.g. plug, gate, stem, etc.) is in a closed position. In one embodiment, the occluding portion 1115 is located proximate to the inlet 1120 of the bladder body 1110 where drain line 1120 is fluidly coupled to the bladder to completely seal off the inlet from the drain line. Although occluding portion 1115 is shown near the top of bladder body 1110 in this example, occluding portion 1115 can be located at another location on bladder body 1110 or multiple occluding portions can be provided. In some less preferred but acceptable alternative embodiments, a flap on inlet 1120 of the bladder body 1120 or other mechanical feature can be used to seal off the flow path from the shunt to the bladder body 1110.

Figure 8:
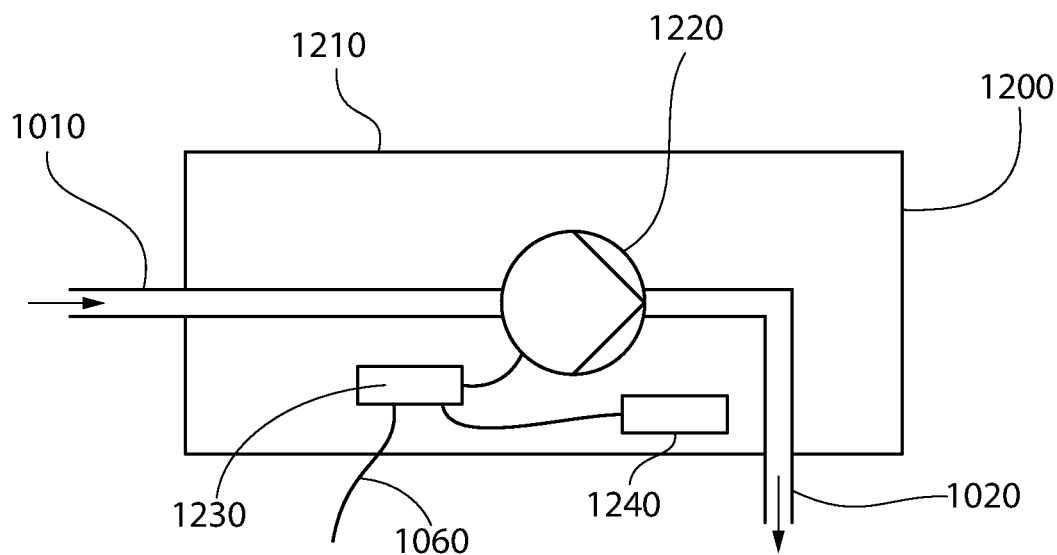
FIG. 8 is a schematic view of a fluid pump in accordance with exemplary embodiments of the invention.

An example of pump unit 1200 is shown schematically in FIG. 8. In this example, pump unit 1200 has a pump body 1210 that houses a pump 1220, an electric pump motor 1230, and a current sensor 1240. Pump 1220 draws CSF from bladder body 1110 through fluid line 1010 when it is directed to do so by controller 1500. In particular embodiments, pump 1220 may be activated for a predetermined period of time at a predetermined flow rate, and then be switched off for a predetermined period of time before being switched back on and repeating the cycle. This cycle provides adequate draining of CSF without requiring ICP.

The foregoing predetermined flow rate and periods of time may be preprogrammed into controller 1500, which in one embodiment controls operation of the pump. Accordingly, the programmable controller 1500 directs the pump 1220 to repeatedly activate and deactivate at a predetermined time interval to draw cerebrospinal fluid from the reservoir 1100 (e.g. collapsible container). Pump unit 1200 can receive a control signal from controller 1500 to turn on or off by a communication link or conduit 1060 which can be, for example, a wire, optical fiber, or a wireless connection. In other possible implementations of the invention, a commercially available liquid detection sensor constructed for in vivo applications, which may be one of the sensors 1140, may alternatively be provided which is operable to detect the presence and accumulation of CSF in the bladder body 1110. The liquid detection sensor is communicably coupled to the controller 1500, which is programmed to activate the pump 1220 for a preprogrammed predetermined period of time to remove the CSF in the bladder body 1110 to the peritoneum 140.

Pump motor 1230 is shown in this example schematically connected to pump 1220 by a curved line for simplicity, recognizing that the connection may in fact be a flexible or rigid straight mechanical connection such as a shaft or a magnetic coupling. Current sensor 1240 measures the actual current drawn by the electric pump motor 1230 during operation of the pump. A current draw that is higher than a normal operating condition can indicate that pump motor 1230 is working harder than normal, which, in turn, can be an indication of a blockage somewhere upstream or downstream of pump 1220, including an indication that bladder body 1110 is collapsed and therefore empty and in the collapsed or occluded condition or state. A higher than normal current draw may in some instances be indicative of a blockage in the drainage passageway between the reservoir 1100 and brain in the drain line 220 and/or shunt 210 itself. Any of these situations where a high current draw is present indicates a condition that should be brought to the attention of the patient and/or the caregiver. The presence of this and other sensed conditions is fed back to controller 1500 by communication conduit 1060 for either triggering an alarm or deactivating the pump unit 1200 if active at the time.

The fluid output of pump 1220 is discharged from pump unit 1200 by way of a fluid line 1020 to a one-way valve 1300. One-way valve 1300 prevents fluid flow from reversing through pump 1220 and back into bladder body 1110.

Valve 1300 may be flow check valve in one example configured for permitting flow in a single direction only. One-way valve 1300 can include a sensor that indicates its position (e.g. open allowing flow or closed blocking flow) and sends that information by way of a communication conduit 1060 to controller 1500. CSF flows from one-way valve 1300 by way of fluid lines 1030 and 1040, and then out of outlet 1050 to a selected in vivo location in the patient's body such as, for example, a cavity such as the peritoneum 140 in the torso. In other embodiments, the outlet 1050 may discharge CSF to an ex vivo collection container outside the patient's body. The fluid lines 1030, 1040 may be single line in which line 1030 represents an upper portion of the line proximate to one-way valve 1300 and line 1040 represents a lower portion of the fluid line proximate to the outlet 1050. A tapping chamber 1400 can be placed in-line at some location in the system. In this example, tapping chamber 1400 is placed downstream of one-way valve 1300, but other locations can also be used. Tapping chamber 1400 provides a space where CSF can collect and that is easily accessible by syringe in order a sample of CSF can be taken. The tapping chamber 1400 may comprise a U-shaped trap or portion of the fluid lines 1030/1040. The configuration of tapping chamber 1400 shown in this example is only one possible configuration. Other configurations can also be used.

Controller 1500 provides control and/or monitoring of the various parts and elements of drainage control system 1000 to which the controller is communicably coupled (e.g. pump unit 1200, one-way valve 1300, etc.). Controller 1500 can be a programmable microcontroller, microprocessor, or other electronic processor-based controller. Controller 1500 is configured and constructed so that it can be implanted (e.g. subcutaneously) and positioned inside the patient's body at a location close enough to the skin to be wirelessly monitored and programmed A technician or health care provider can use a programmer/interrogator held within a certain distance of controller 1500 (or an antenna of controller 1500) to communicate with controller 1500 in order to program/reprogram controller 1500 and/or download data from controller 1500. All settings of the system can be modified after the system is implanted in the patient. Non-exclusive examples of programming or reprogramming include setting or modifying the various wait times (periods of time), setting or modifying the pump run time, setting or modifying the acceptable ranges of the various sensor, turning on/off a particular sensor, resetting alarm conditions, setting or modifying what type of alarms correspond to each alarm condition, etc.

In addition to the various sensors discussed in this disclosure, other sensors such as, for example, a heart rate sensor, a blood pressure sensor, or a respiratory rate sensor, can be provided to monitor a stress condition of the patient. These sensors may be communicably coupled to controller 1500 for transmitting data and control signals back/forth to these sensors.

Controller 1500 includes configurable control circuitry operable to execute program instructions or code (e.g. control logic or software). The controller 1500 may comprise one or more programmable microprocessors, non-transitory tangible computer readable medium, programmable input/output peripherals, and all other usual appurtenances typically associated with a controller to form a fully functional control system. Computer readable medium may include volatile memory and non-volatile memory operably and communicably coupled to the processor(s). Any suitable combination and types of volatile or non-volatile memory may be used including as examples, without limitation, random access memory (RAM) and various types thereof, read-only memory (ROM) and various types thereof, flash memory, or other memory which may be written to and/or read by the processor operably connected to the medium. Both the volatile memory and the non-volatile memory may be used for storing the program instructions or software. A programmable controller of the foregoing type is a commercially available known device of certain structure in the art. In some embodiments, the controller may be a system on a chip (SOC) or an application-specific integrated circuit (ASIC) comprising a microchip; either of which may be designed and configured for control of the CSF drainage system.

The controller 1500 further includes an input/output communication interface or module configured for wireless and/or wired communication for programming the controller and exchanging data therewith. Wireless communication protocols used may include Bluetooth, NFC (near field communication), or others. The controller includes all the usual ancillary components known to those skilled in the art as necessary to form a fully functional data processing and control device. It is well within the ambit of one skilled in the art to provide and configure the controller 1500 with all these required appurtenances to control operation of drainage control system 1000 in accordance with the functionality described herein. It will be appreciated that various aspects of the controller and drainage control system may be embodied in software, firmware, and/or hardware.

Controller 1500 and pump motor 1230 require an energy source such as a battery. In one embodiment, a lithium ion or other type single use or rechargeable battery may be provided. In order to avoid surgical replacement of batteries, wireless charging technology can be utilized to recharge the rechargeable batteries. This can include, for example, inductive charging.

Also shown in FIG. 4 is a level sensor 1600. Level sensor 1600 determines the orientation of the patient such as, for example, whether the patient is generally vertical (standing up or sitting) or horizontal (laying down or reclining) The orientation of the patient is important because intracranial pressure (ICP) can vary depending on the orientation of the patient. An increase in ICP while the patient is horizontal can indicate an abnormal and possibly dangerous condition. On the other hand, a temporary increase in ICP when the patient is standing or partaking in strenuous activity is normal. The level sensor can prevent a false alarm in the case of this temporary increase in ICP when the patient is standing or partaking in strenuous activity. In some embodiments, an elevated ICP is an alarm condition only when the patient is horizontal. Particular embodiments can define "vertical" and "horizontal" as being within a certain range of angles relative to vertical or horizontal. For example, all conditions within 10 degrees of horizontal will be considered horizontal. Other ranges of angles can also be used.

Figure 9:
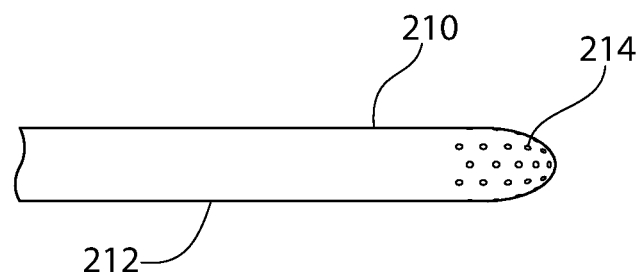
FIG. 9 is a partial view of a shunt in a non-clogged state in accordance with exemplary embodiments of the invention.
Figure 10:
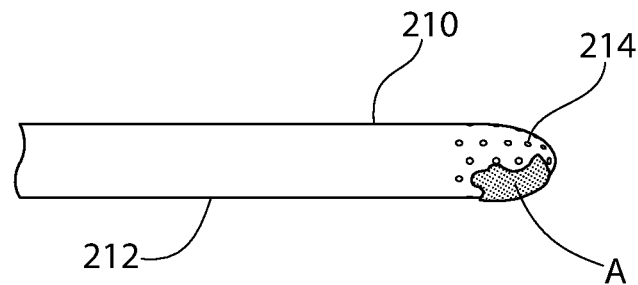
FIG. 10 is a partial view of a shunt in a clogged state in accordance with exemplary embodiments of the invention.

FIGS. 9 and 10 show an example of a tubular shunt 210. In these examples, a terminal end of shunt 210 has a plurality of apertures 214 that allow CSF to flow from the ventricle to drain line 220. FIG. 9 shows a normally operating shunt 210 with un-blocked apertures 214. FIG. 10 shows an example of a condition where some apertures 214 are blocked by a blockage A. Some blockages are acceptable as they do not block the flow of CSF to present a problem. However, a blockage that restricts the flow of CSF beyond a certain point can be dangerous to the patient and requires notice to the patient and/or caregiver. Significant blockage of apertures 214 will result in pump 1220 having to work harder, which will result in an increase in current draw by pump 1220. As explained above, this increased current draw can be sensed by controller 1500, and if required, the controller can initiate an alarm condition and/or terminate operation of the pump unit 1200 if active.

The various elements of drainage control system 1000 work together to provide a system that removes excess CSF from the brain of patients, including NPH patients, and monitors the drainage process to increase the safety of the patient.

Figure 11:
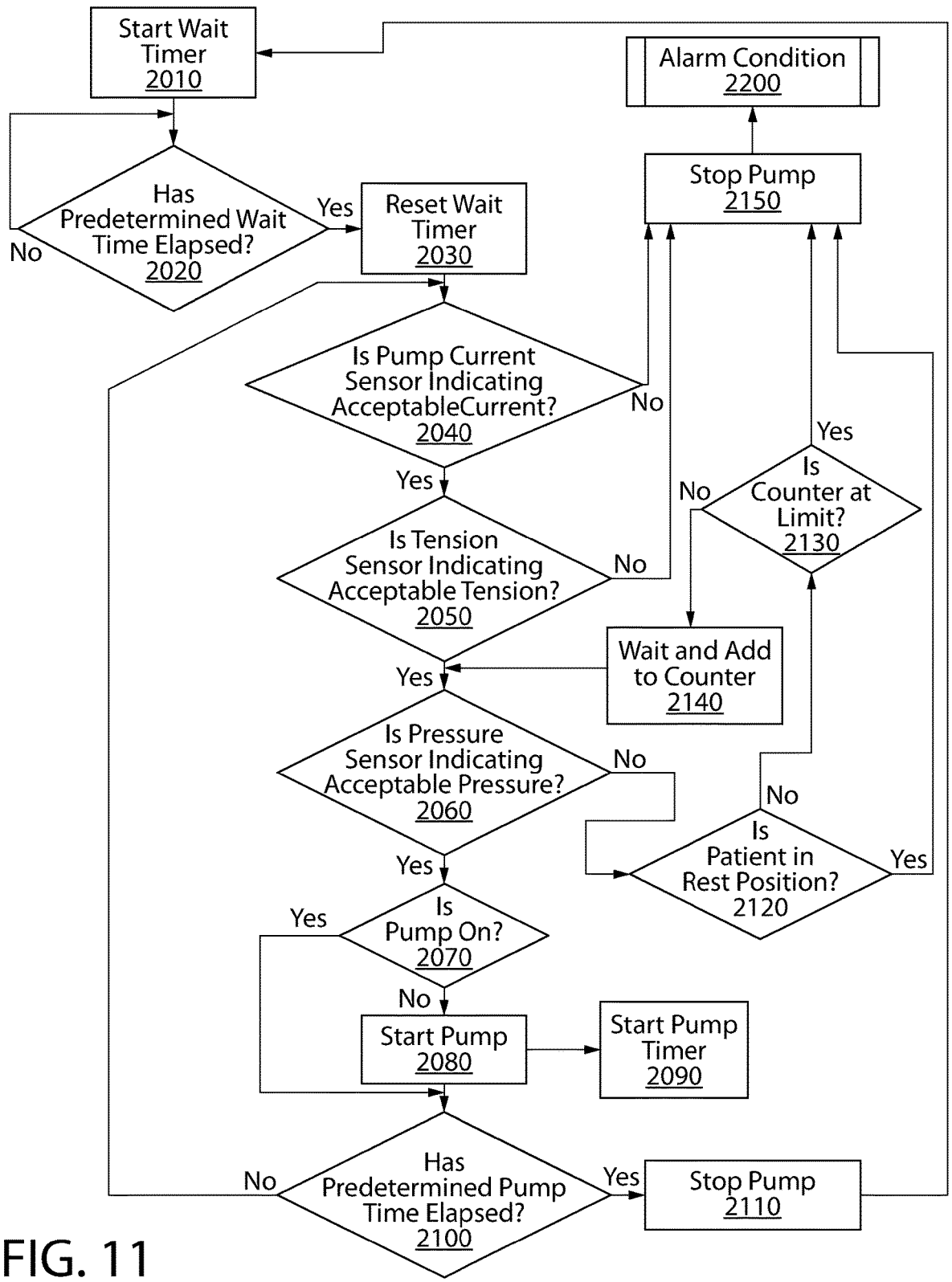
FIG. 11 is a flow chart showing a method in accordance with exemplary embodiments of the invention.
Figure 12:
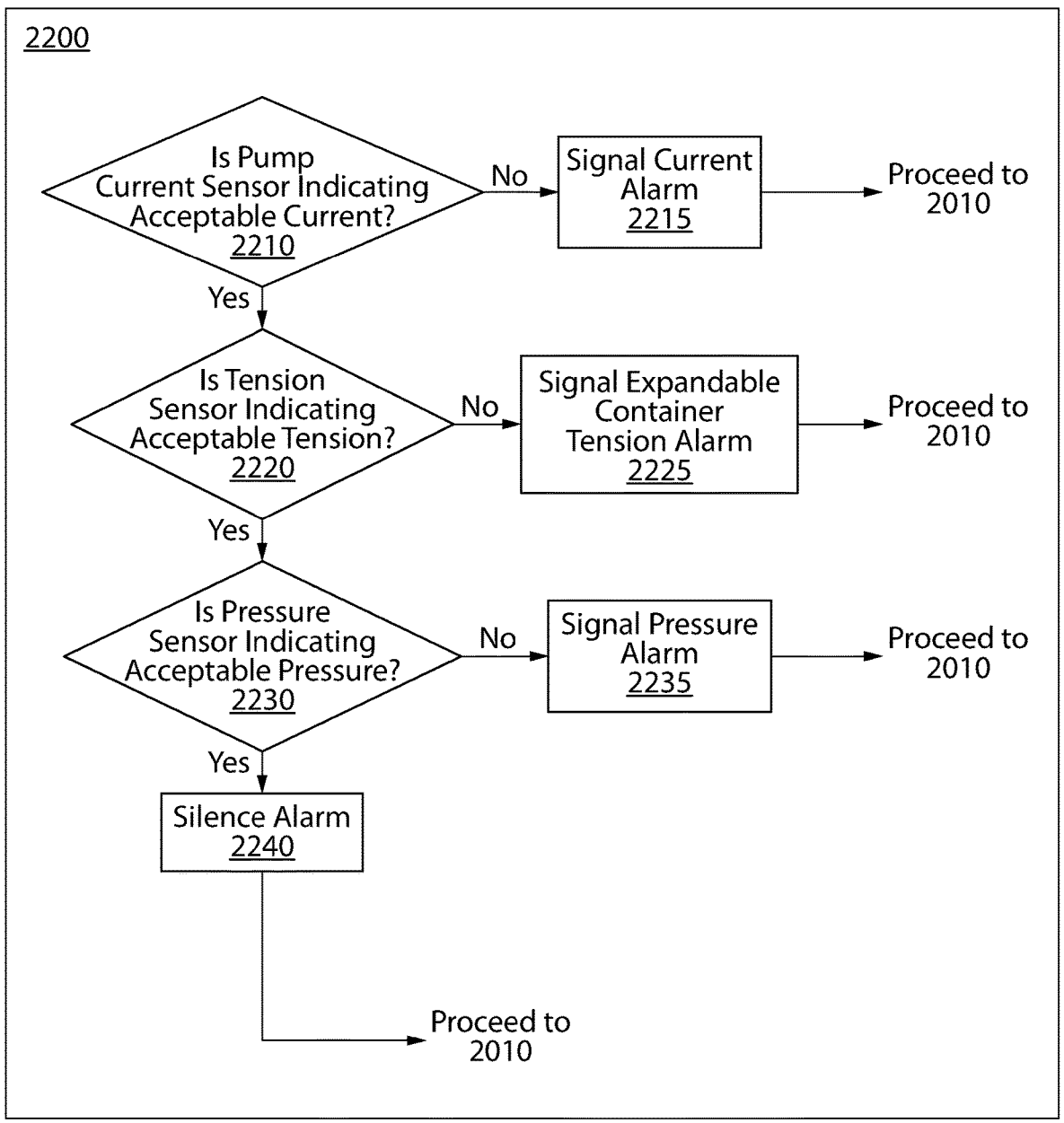
FIG. 12 is a flow chart showing a sub-section of the flow chart of FIG. 11

FIGS. 11 and 12 are flow charts of control logic or program instructions preprogrammed into controller 1500 that show an example of how drainage control system 1000 can be configured to operate under the control of the controller. Controller 1500 thus automatically controls and performs the steps described below associated with a method/process of draining cerebrospinal fluid from the brain of a patient. Other combinations of the elements or steps shown in FIGS. 11 and 12 can be used, as well as additional elements/steps or fewer elements/steps. In the example method/process, the drainage control system 1000 is configured to include sensors 1140 comprising a stretch sensor, pressure sensor, and current sensor. More, less, and/or other types of sensors may be used.

In FIG. 11 a wait timer is started at 2010 by controller 1500. The wait timer will determine when a preprogrammed predetermined wait time period between cycles of pump 1220 has expired. The progress of the wait timer is monitored by the controller at 2020. At the conclusion of the predetermined wait period, the wait timer is reset at 2030 and then processing is continued with the monitoring of various sensors to determine whether various conditions exist.

At 2040 if the current sensor 1240 indicates a current outside of the preprogrammed acceptable range, the pump is stopped at 2150 and an alarm condition is indicated at 2200. A current draw outside of a normal range can indicate a blockage in the system upstream/downstream of the pump, and/or a malfunctioning pump among other things. Either of these conditions requires notification of the patient and/or caregiver by the controller 1500 which activates a visual and/or audible alarm.

In particular embodiments, whether the pump is stopped or not can be dependent on more than just a simple increase in the current draw. In one example, the current draw can be compared to a preprogrammed occluded threshold (equal to the current draw seen when bladder body 1110 is collapsed) and a normal current draw. If the current draw is above the normal current draw but below the occluded threshold, then the pump should continue to run, but an alarm should be signaled. In another example, the profile of the current draw over time can be monitored to see how rapidly the current draw increased. A rapid current draw increase can indicate a collapsed bladder, whereas a gradual current draw increase can indicate a partial blockage at some point in the system. In another example, when an increased current draw is sensed, another sensor that senses collapsing of the bladder (for example the tension sensor) is interrogated. If the tension sensor indicates a collapsed bladder, then it is likely that the increased current draw is not due to a blockage in the system or a malfunctioning pump.

At 2050 if the tension sensor indicates a tension in the bladder body outside of the preprogrammed acceptable range, the pump is stopped at 2150 and an alarm condition is indicated at 2200. A bladder body tension above a normal range can indicate stretching of the bladder body as a result of above normal pressure in the bladder body. Above normal pressure in the bladder body can indicate increase ICP. Because increased ICP, in some embodiments, can be normal for a given orientation of the patient or as a result of strenuous activity, a time delay and a check of the orientation of the patient can be added to the processing. As a result, a processing loop similar to 2120-2140 can be added between 2050 and 2150 in some embodiments. Once the delay and orientation are satisfied, if applicable, and an above normal tension still exists, the pump is stopped at 2150 and the alarm condition is indicated at 2200.

At 2060 if the pressure sensor indicates a pressure in the bladder body outside of the preprogrammed acceptable range, a processing loop inserts a preprogrammed time delay and the controller 1500 checks the orientation of the patient. The pump is stopped at 2150 and an alarm condition is indicated at 2200. Above normal pressure in the bladder body can indicate increase ICP. Because increased ICP, in some embodiments, can be normal for a given orientation of the patient or as a result of strenuous activity, a time delay and a check of the orientation of the patient can be helpful. At 2120, the orientation of the patient is determined by, for example, the level sensor 1600 communicably coupled to the controller (see, e.g. FIG. 4). If the orientation of the patient indicates that the patient is in a rest position (e.g. generally horizontal position), the pump is stopped at 2150 and an alarm condition is indicated at 2200. If the orientation of the patient indicates that the patient is not in a rest position (e.g. generally vertical position), then a preprogrammed time delay counter is checked at 2130. In one embodiment, the delay counter may be automatically initiated by controller 1500 when an unacceptable pressure is first sensed at 2060 (i.e. a "no" response). At 2130, if the preprogrammed time delay counter limit has not expired ("no" response), then control passes to 2140 to wait and the pressure is re-checked at 2060. The delay counter provides a delay before stopping the pump and indicating an alarm condition in order to check to see if the pressure returns to normal within the preprogrammed predetermined time delay limit. Normal, non-alarming situations (strenuous activity, for example) can cause a temporary increase in pressure. If the pressure returns to an acceptable range before the delay counter expires, processing continues to 2070. If the pressure remains outside of the acceptable range after the predetermined delay has expired at 2130, the pump is stopped at 2150 and an alarm condition is indicated at 2200.

If none of the sensors indicate the existence of a parameter outside of the acceptable ranges, processing continues to 2070 where the controller 1500 determines if the pump 1220 is already running If the pump is not running, the pump is started at 2080 by the controller and the pump timer is started at 2090 which controls the run time of the pump. Once started, the pump runs for a preprogrammed predetermined time at a predetermined flowrate to pump a predetermined volume of CSF from the reservoir 1100 to the peritoneum 140. The operation of pump 1220 (i.e. active/on or inactive/off) and duration of the pump timer is thus controlled by the controller. If instead the controller determines that the pump is already running at 2070, or once the pump is started at 2080, a determination is made by the controller at 2100 as to whether the predetermined pump run time (e.g. pump timer) has elapsed. If the predetermined pump run time has elapsed, the pump is stopped at 2110 and processing returns to 2010 to begin the cycle again. If the predetermined pump run time has not elapsed at 2100, processing continues by repeating the monitoring of the sensors, beginning at 2040.

By using the foregoing process, it is apparent that the pump unit 1200 can be programmed via controller 1500 to drain CSF from reservoir 1100 at precise predetermined volumes and flow rates via activating and deactivating the pump at preprogrammed time intervals. The pump is run for a predetermined period of run time at the desired flowrate to extract the desired volume of CSF from the reservoir over a period of time. The pump is then in a standby deactivated state for the duration of the wait time until the next cycle of operation as described above and in FIG. 11. The controller 1500 may be programmed by the medical personnel to change the pumping flowrate, wait period, and run time as needed if condition of the patient changes affecting the accumulation of CSF in the brain, thereby advantageously providing an extremely flexible drainage control system. In addition, the fluid coupling of the deformable collapsible reservoir between the brain and pump provides a safeguard against exerting a negative pressure on the brain by the pump.

An example of the processing associated with an alarm condition at 2200 is shown in FIG. 12. The example shown in FIG. 12 determines which sensor is detecting an abnormality and signals the corresponding alarm. The controller controls the alarms and determines what type of alarm is to be activated based on which sensor is detecting an alarm condition. For example, a particular alarm condition may warrant an audible, visible, or vibratory alarm, or any combination of these or other types of alarms.

At 2210 it is determined whether the pump current sensor is in an alarm state. If it is, then a current alarm is signaled at 2215 and then processing continues to 2010. At 2220 it is determined whether the tension sensor is in an alarm state. If it is, then a collapsible container tension alarm is signaled at 2225 and then processing continues to 2010. At 2230 it is determined whether the pressure sensor is in an alarm state. If it is, then a pressure alarm is signaled at 2235 and then processing continues to 2010. If none of these sensors indicate an alarm condition, then no alarm is activated and/or any alarm that was activated is silenced at 2240. 2240 will silence an alarm that was properly activated but is no longer needed because the condition which triggered the alarm has been corrected. This allows for temporary alarm conditions to be brought to the attention of the patient and/or caregiver while also silencing the alarm once the temporary alarm condition passes.

The alarm can be visual such as a light that is visible through the skin, audible, or a combination of both. The alarm can also or alternatively be transmitted to an external device such as a medical alert bracelet, a hospital monitoring device, or a cellular phone of other electronic device.

The processing shown in FIGS. 11 and 12 are just one example of an embodiment of the invention. It is noted that other combinations of steps and other elements can be provided while still staying within the spirit and scope of the invention. For example, fewer or more sensors of similar or different types can be used in different or similar combinations and orders, and different operations can be dictated when an alarm condition is sensed.

In some cases, for example in a HPH patient, it may be desirable to keep the pump running even though a sensor has detected an abnormal condition. For example, when the pump current sensor indicates an increased resistance to outflow this might be indicating a distal shunt obstruction. In this circumstance, it may be desirable to signal an alarm but continue pump operation because it may still be possible to remove CSF from the brain. As another example, if pressure is high in a HPH patient, it can be desirable to signal an alarm but continue pump operation to remove CSF from the brain. Because other alarm conditions can exist where it is desirable to continue pump operation, the alarm conditions and pump operation are programmable and reprogrammable after the system is implanted in the patient.

It bears noting that all of the components of CSF drainage system 1000 shown within or crossing the dashed box in FIG. 4 are preferably configured and constructed of biocompatible materials suitable for in vivo implantation in the patient in a preferred embodiment.

While the foregoing description and drawings represent exemplary embodiments of the present disclosure, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made within the scope of the present disclosure. One skilled in the art will further appreciate that the embodiments may be used with many modifications of structure, arrangement, proportions, sizes, materials, and components and otherwise, used in the practice of the disclosure, which are particularly adapted to specific environments and operative requirements without departing from the principles described herein. The presently disclosed embodiments are therefore to be considered in all respects as illustrative and not restrictive. The appended claims should be construed broadly, to include other variants and embodiments of the disclosure, which may be made by those skilled in the art without departing from the scope and range of equivalents. In addition, all combinations of any and all of the features described in the disclosure, in any combination, are part of the invention.

What is claimed is:

1. A system for draining cerebrospinal fluid from a bodily cavity of a patient, the system comprising:
   a collapsible container configured to be fluidly connected to a shunt that is located in the bodily cavity in a head of the patient for draining cerebrospinal fluid;
   a drain line fluidly coupling the shunt directly to the collapsible container, the drain line forming a single inlet into the collapsible container;
   a pump fluidly connected to the collapsible container; and
   a programmable controller that directs the pump to repeatedly activate and deactivate to draw cerebrospinal fluid from the collapsible container;
   the collapsible container being located remotely from the bodily cavity to be drained such that there is no contact between the collapsible container and bodily cavity;
   wherein the collapsible container is interposed between the drain line and the pump;
   wherein a blockage in the drain line or shunt upstream of the collapsible container when the pump is operating causes the collapsible container to collapse and fluidly isolate the pump from the bodily cavity to prevent subjecting tissue surrounding the bodily cavity to negative pressure generated by the pump.

2. The system according to claim 1, wherein the collapsible container is a resiliently-deformable flexible bladder having a variable volume, the bladder configured to expand or contract depending on a volume of the cerebrospinal fluid in the bladder.

3. The system according to claim 2, wherein the bladder includes an occluding portion structured to collapse to a greater degree than other parts of bladder when a negative pressure forms within the bladder.

4. The system according to claim 3, wherein the occluding portion is operable to completely fluidly isolate the bladder from a fluid passageway coupled to the shunt to prevent subjecting tissue surrounding the bodily cavity to negative pressure.

5. The system according to claim 2 wherein the bladder is formed of a biocompatible material and configured for implantation in the patient.

6. The system according to claim 1, wherein the pump draws cerebrospinal fluid from the collapsible container at a predetermined flow rate and predetermined period of time each preprogrammed into the controller.

7. The system according to claim 1, further comprising a level sensor operably coupled to the controller for indicating an orientation of the patient.

8. The system according to claim 1, wherein the pump is an electric pump which draws a current from a power source.

9. The system according to claim 8, further comprising a current sensor operably coupled to the pump and controller, the controller configured to compare an actual measured current draw to a preprogrammed acceptable current range and deactivate the pump if the actual measured current draw is outside the acceptable current range.

10. The system according to claim 2, further comprising a tension sensor attached to the bladder and communicably coupled to the controller, the tension sensor operable to measure an actual tension in a body of the bladder.

11. The system according to claim 10, wherein the controller is configured to compare the actual tension to a preprogrammed acceptable tension range and deactivate the pump if the actual tension is outside the acceptable tension range.

12. The system according to claim 10, further comprising a pressure sensor operable to measure an actual pressure of cerebrospinal fluid in the bladder.

13. The system according to claim 1, wherein the bodily cavity is a ventricle in a brain of the patient.

14. The system according to claim 1, wherein the programmable controller activates and deactivates the pump at a predetermined time interval programmed into the controller.

15. A method for draining cerebrospinal fluid from a bodily cavity of a patient, the method comprising:
 implanting a shunt in the bodily cavity which is in a head of the patient;
 draining the cerebrospinal fluid from the shunt emplaced in the bodily cavity via a drain line fluidically coupling the shunt directly to a deformable collapsible container, the drain line forming a single inlet into the collapsible container, the collapsible container located remotely from the bodily cavity to be drained such that there is no contact between the collapsible container and bodily cavity, the collapsible container changeable between a collapsed state and an expanded state;
 pumping the cerebrospinal fluid from the collapsible container with a pump fluidly connected to the collapsible container;
 wherein the collapsible container is interposed between the drain line and the pump;
 repeatedly activating and deactivating the pump at a predetermined time interval with a programmable controller;
 a negative pressure forming in the collapsible container, and the collapsible container collapsing in response to a blockage in the drain line or shunt upstream of the collapsible container and fluidly isolating the collapsible container and pump from the shunt to prevent subjecting tissue surrounding the bodily cavity to the negative pressure.

16. The method according to claim 15, further comprising sensing an actual tension in a body of the collapsible container with a tension sensor communicably coupled to the programmable controller, the programmable controller configured to compare the actual tension to a preprogrammed acceptable range of tension, the programmable controller deactivating the pump based on the comparison of the actual tension to the acceptable range of tension.

17. The method according to claim 15, wherein the bodily cavity is a ventricle in a brain of the patient.

* * * * *